United States Patent [19]

Trenzeluk

[11] Patent Number: 4,855,138
[45] Date of Patent: Aug. 8, 1989

[54] SKIN THERAPEUTIC MIXTURE CONTAINING MATICO EXTRACT

[75] Inventor: Theodore Trenzeluk, Manville, N.J.

[73] Assignee: Tecma Laboratories, Inc., Manville, N.J.

[21] Appl. No.: 877,777

[22] Filed: Jun. 24, 1986

[51] Int. Cl.⁴ .................. A61K 35/78; A61K 33/30; A61K 31/385; A61K 31/20

[52] U.S. Cl. .................. 424/195.1; 424/DIG. 13; 424/642 W; 514/439; 514/558; 514/724; 514/859; 514/863; 514/928

[58] Field of Search ............ 424/145, 195.1, DIG. 13; 514/859, 863, 439

[56] References Cited

U.S. PATENT DOCUMENTS

| | | | |
|---|---|---|---|
| 112,329 | 3/1881 | Field | 424/159 |
| 230,365 | 7/1880 | Watts | 424/195.1 |
| 915,781 | 3/1909 | Marshall | 424/195.1 |
| 1,519,755 | 12/1924 | Chapman | 424/195.1 |
| 1,627,963 | 5/1927 | Fuller | 424/195.1 |
| 2,370,561 | 2/1945 | Mecca | 514/106 |
| 2,843,522 | 7/1958 | Mahon | 424/145 |
| 3,878,197 | 4/1975 | Maret et al. | 424/195.1 |
| 3,892,853 | 7/1975 | Cobble | 424/195.1 |
| 3,920,816 | 11/1975 | Seegall et al. | 514/970 |
| 4,178,372 | 12/1979 | Coats | 424/195.1 |
| 4,215,049 | 7/1980 | Takahashi et al. | 268/343.3 |
| 4,258,035 | 3/1981 | Spies | 424/195.1 |
| 4,302,443 | 11/1981 | De Navarre et al. | 424/68 |
| 4,369,180 | 1/1983 | Mihalovits | 514/2 |
| 4,446,131 | 5/1984 | Maughan | 424/195.1 |
| 4,474,751 | 10/1984 | Haslam et al. | 424/78 |
| 4,505,902 | 3/1985 | Millard | 424/195.1 |

Primary Examiner—John W. Rollins
Attorney, Agent, or Firm—R. Martin Oliveras

[57] ABSTRACT

According to the present invention, a skin therapeutic mixture is useful for the alleviation of certain skin disorders such as acne, psoriasis, burns, pimples, blackheads, and open sores, and such mixture comprises: the therapeutic agent being the extract from the dried leaves of the Matico plant; a preservative chosen from the group consisting of a sulfaderivative such as sulfathiazole and an alcohol amine; a skin softener such as an oil; and an oil soluble base. An inert pigment such as zinc oxide and a fragrance such as a perfume may be added. According to a specific illustrative embodiment of the present invention, the skin therapeutic mixture comprises about 2% to 35% by weight of the extract from the dried leaves of the Matico plant as the therapeutic agent; about 2% to 15% by weight of sulfathiazole as the preservative; about 5% to 10% by weight of zinc oxide as the inert white pigment, and about 40% to 91% by weight of petrolatum.

3 Claims, No Drawings

SKIN THERAPEUTIC MIXTURE CONTAINING MATICO EXTRACT

FIELD OF THE INVENTION

This invention relates to skin therapeutic preparations and in particular to such preparations which include the extract from the dried leaves of the Matico plant as the therapeutic agent.

SUMMARY OF THE PRESENT INVENTION

A summary and features of the present invention are therefore that:

a. according to the present invention, a skin therapeutic mixture for alleviation of the aforementioned skin conditions comprises the therapeutic agent being the extract from the dried leaves of the Matico plant, a preservative chosen from the group consisting of a sulfa derivative such as sulfathiazole and an alcohol amine, a skin softener such as an oil, and an oil soluble base;

b. an inert pigment such as zinc oxide and a fragrance such as a perfume may be added to the mixture;

c. according to a first illustrative embodiment of the present invention, the skin therapeutic mixture comprises the extract from the dried leaves of the Matico plant as the therapeutic agent, sulfathiazole as the preservative, zinc oxide as a white inert pigment, and petrolatum as the base;

d. according to a second illustrative embodiment of the present invention, the skin therapeutic mixture comprises a water phase, an oil phase, and perfume as the fragrance, said water phase further comprising the extract from the leaves of the Matico plant, glycerol, sodium lauryl sulfate, tri-ethanol amine, and water; and said oil phase further comprising palmitic acid and cetyl alcohol; and e. according to a third illustrative embodiment of the present invention, the skin therapeutic mixture comprises a water phase, an oil phase, and perfume as the fragrance, said water phase further comprising the extract from the dried leaves of the Matico plant, tri-ethanol amine, propylene, glycol, propyl p-hydroxy benzoate, and water; and said oil phase further comprising stearic acid, cetyl alcohol, glycerol monosterate, and propyl p-hydroxy benzoate.

An advantage of the present invention is that when applied to the skin surface it is also absorbed into the skin and is able to contact the subject lesion.

DISCUSSION OF THE PRIOR ART

Several prior art patents disclose medical or therapeutic mixtures as follows:

Field U.S. Pat. No. 112,329 entitled "Improvement In Medical Compounds For Cure Of Catarrh And Asthma" discloses a solution comrising water, potassium nitrate, potassium chlorate, licorice extract, boneset leaves, hemp leaves, stromonium leaves, cabela leaves, Virginia snake root, and gum myrrh;

Watts U.S. Pat. No. 230,365 entitled "Liniment" disclose a liniment comprising wild cherry, wild thistle, spearmint, coal oil, turpentine, peppermint, bicarbonate of soda, ammonia, and camphor;

Marshall U.S. Pat. No. 915,781 entitled "Hair Tonic" discloses a hair tonic consisting of an intimate mixture of olive oil in an aqueous extract of the leaves of elder, crab apple, morning glory, night shade, wild sage, horseradish, boneset, and sheep sorrel;

Chapman U.S. Pat. No. 1,519,755 entitled "Powdered Preparation For Poultices" discloses a poultice preparation composed of a mixture of dry powdered vegetable materials including boneset, sweet fern, and a glutinous material;

Fuller U.S. Pat. No. 1,627,963 entitled "Medicinal Product" discloses a fluid extract and tincture comprising a vegetable drug used as a remedial agent and a halogen containing ester of glycerine;

Mecca U.S. Pat. No. 2,370,561 entitled "Therapeutic Product And Method Of Making Same" discloses a therapeutic product comprising the active molecular structure of allantoin and a sulfa compound;

Mahon U.S. Pat. No. 2,843,522 entitled "Perianal Ointment" discloses a water repellant perianal ointment comprising petrolatum, para di-isobutyl cresoxy ethyl di-methyl benzyl ammonium chloride, and calcium caseinate;

Maret U.S. Pat. No. 3,878,197 entitled "Process For Preparing Extracts Of Aloe Vera" discloses the process comprising the steps of cutting the rind and aloins of an aloe vera leaf from the gel, and agitating the gel under ultraviolet radiation in a digestion liquid containing amine, phosphorus ions, and potassium ions at a given pH;

Cobble U.S. Pat. No. 3,892,853 entitled "Stabilized Aloe Vera Gel And Preparation Of Same" discloses the process comprising the steps of mechanical separation, homogenization, addition of hydrogen peroxide, heating to a given temperature, addition of an effective preparation of a nontoxic oxidant, and addition of an effective preparation of a nontoxic buffer to maintain a given pH range;

Seegall et al U.S. Pat. No. 3,920,816 entitled "Composition For Treating Respiratory Diseases" discloses a composition consisting of the juice from the freshly cut leaves of the plant aloe arborescens obtained by extracting the leaves in boiling bees honey; enAy. Coats U.S. Pat. No. 4,178,372 entitled "Hypoallergenic Stabilized Aloe Vera Gel" discloses a process comprising the steps of mechanical separation, extrusion, heating to a given temperature range, addition of a catalytic amount of hydrogen peroxide, addition of ascorbic acid, and addition of citric acid to maintain a given pH range;

Takahaski et al U.S. Pat. No. 4,215,049 entitled "Antitumorgenic Lactone Derivative" discloses a hiyodorilacton-B having a given formula;

Spies U.S. Pat. No. 4,258035 entitled "Method And Compound For Treatment of Arthritic Conditions In Dogs" discloses a mixture of herbal components consisting essentially of camfrey, mullin, fenugeek, nettle, broom tops, and boneset;

De Navarre U.S. Pat. No. 4,302,443 entitled "Non Irritating Anti-Perspirant" discloses a composition comprising aluminum chlorohydroxide and an extract of the aloe vera plant;

Mihalovits U.S. Pat. No. 4,369,180 entitled "Cosmetic Facial Preparation Containing Aloe Vera" discloses a preparation comprising aloe vera, citric acid, potassium sorbate, sodium benzoate, cornstarch, albumin, hydroxy propyl methly cellulose, allantoin, vitamin A, vitamin D2, and vitamin E;

Maughan U.S. Pat. No. 4,446,131 entitled "Controlled Temperature Process For Manufacturing Of Improved Stabilized Aloe Vera" discloses a process comprising the steps of heating to a given temperature range, addition of ascorbic acid, maintaining the mixture within a given temperature range, and cooling to ambient temperature in less than one hour;

Haslam et al U.S. Pat. No. 4,474,751 entitled "Ophthamlic Drug Delivery System Utilizing Thermosetting Gels" discloses an aqueous composition comprising a given polymer by formula, a pharmaceutic or diagnostic agent, and a pharmaceutically acceptable acid or base to adjust the pH within a certain range; and Millard U.S. Pat. No. 4,505,902 entitled "Skin Treatment Preparation" discloses a preparation comprising mineral oil, apricot kernal oil, avocado oil, cod liver oil, propylparaben, and butylated hydroxy anisole.

The above cited prior art patents do not appear to disclose the subject skin therapeutic mixture including the extract from the dried leaves of the Matico plant as the therapeutic agent.

Objects of the present invention used therefore to provide a skin therapeutic mixture:

for the alleviation of certain skin disorders;
with few known side effects;
that does not irritate the skin;
for treatment of the skin to provide moisture thereto, to promote healing, and to maintain a healthy condition;
for the alleviation of acne, psoriasis, burns, pimples, blackheads, and open sores.

DETAILED DESCRIPTION

The above and other objects, features, and advantages of the present invention will be better appreciated from a reading of the following detailed description.

According to the present invention, the skin therapeutic mixture comprises the extract from the dried leaves of the Matico plant, a preservative, and an oil soluble base. The leaves of the Matico plant are dried under moderate light, under warm temperatures, and with frequent tossing. The dried leaves are then ground to a very small particle size, and thereafter are extracted with water. The smaller the particle size, the more complete will be the extraction.

The following examples are illustrative of suitable skin therapeutic mixtures containing the extract from the dried leaves of the Matico plant:

Example #1

| Component | Percentage By Weight |
| --- | --- |
| Extract from the dried leaves of the Matico plant | 2% to 35% |
| Sulfathiazole | 2% to 15% |
| Zinc oxide | 5% to 10% |
| Petrolatum | 40% to 91% |

In this example the extract and the other ingredients may be blended together most efficiently by warming the petrolatum with moderate stirring to a semi liquid, then adding the zinc oxide, sulfathiazole, and the extract in that order. The mixture should be stirred in this fashion for about 10 minutes to insure uniformity of the product. The lower limits are chosen to provide desired minimum effectiveness and the upper limits are limited by the ability to prepare a mixture being suitable for external skin application.

Example #2

| Component | Percentage By Weight |
| --- | --- |
| A. Water Phase | |
| Extract from the dried leaves of the Matico plant | 10 |
| Glycerol | 2 |
| Sodium lauryl sulfate | .2 |
| Tri-ethanol amine | .8 |
| Water | 83 |
| B. Oil Phase | |
| Palmitic acid | 3 |
| Cetyl alcohol | .5 |
| C. Perfume for fragrance as needed | .5 |

In this example, the water and oil phases are heated separately while stirring at moderate shear speeds to 75 degrees C. Then add the oil phase to the water phase very slowly to insure good dispersion. The smaller the oil stream in the water, the better the dispersion. Fragrance is then added while stirring in small amounts of the same as needed.

Example #3

| Component | Percentage By Weight |
| --- | --- |
| A. Water phase | |
| Extract from the dried leaves of the Matico plant | 8.5 |
| Tri-ethanol amine | .95 |
| Propylene glycol | 4.8 |
| Propyl p-hydroxy benzoate | .2 |
| Water | 80 |
| B. Oil phase | |
| Stearic acid | 3 |
| Cetyl alcohol | .6 |
| Glycerol monosterate | 1 |
| Propyl p-hydroxy benzoate | .06 |
| C. Perfume for fragrance as needed | |

In this example, heat the water and oil phase separately to 75 degrees C. Then stir the water phase at moderate shear speeds while adding the oil phase slowly to the water phase.

Several formulations according to the present invention have been tested on animals and humans. The mixtures were found to be nontoxic. The mixtures were tried on over 500 patients for several skin conditions such as psoriasis and others.

While the arrangement according to the present invention has been described in terms of specific illustrative embodiments, it will be apparent to those skilled in the art that many modifications are possible within the spirit and scope of the disclosed principle.

What is claimed is:

1. A mixture for alleviating the skin conditions of acne, psoriasis, burns, pimples, blackheads, and open sores, said mixture comprising:
    a. the aqueous extract from the leaves of the Matico plant, said aqueous extract being prepared as follows: said leaves are dried under moderate light, under warm temperature, and with frequent tossing; then said dried leaves are ground to a very small particle size; and then said ground leaves are extracted with water; said aqueous extract being about 2% to about 35% by weight of said mixture;
    b. a preservative being sulfathiazole, wherein said preservative is about 2% to about 15% by weight of said mixture;

c. an inert pigment being zinc oxide, said inert pigment being about 5% to about 10% by weight of said mixture; and
d. an oil soluble base being petrolatum, said oil soluble base being about 40% to about 91% by weight of said mixture.

2. A mixture for alleviating the skin conditions of acne, psoriasis, burns, pimples, blackheads, and open sores, said mixture comprising:
a. the aqueous extract from the leaves of the Matico plant, said aqueous extract being prepared as follows: said leaves are dried under moderate light, under warm temperature, and with frequent tossing; then said dried leaves are ground to a very small particle size; and the said ground leaves are extracted with water; said aqueous extract being about 10% by weight of said mixture;
b. a preservative being tri-ethanol amine, wherein said preservative is about 0.8% by weight of said mixture;
c. glycerol being about 2% by weight of said mixture;
d. sodium lauryl sulfate being about 0.2% by weight of said mixture;
e. palmitic acid being about 3% by weight of said mixture;
f. cetyl alcohol being about 0.5% by weight of said mixture;
g. a fragrance being about 0.5% by weight of said mixture; and
h. water being about 83% by weight of said mixture.

3. A mixture for alleviating the skin conditions of acne, psoriasis, burns, pimples, blackheads, and open sores, said mixtures comprising:
a. the aqueous extract from the leaves of the Matico plant, said aqueous extract being prepared as follows: said leaves are dried under moderate light, under warm temperature, and with frequent tossing; then said dried leaves are ground to a very small particle size; and then said ground leaves are extracted with water; said aqueous extract being about 8.5% by weight of said mixture;
b. a preservative being tri-ethanol amine, wherein said preservative is about 0.95% by weight of said mixture;
c. propylene glycol being about 4.8% by weight of said mixture;
d. propyl p-hydroxy benzoate being about 0.26% by weight of said mixture;
e. stearic acid being about 3% by weight of said mixture;
f. cetyl alcohol being about 0.6% by weight of said mixture;
g. glycerol monosterate being about 1% by weight of said mixture;
h. water being about 80% by weight of said mixture; and
i. a fragrance being the balance by weight of said mixture.

* * * * *